US012383593B2

(12) United States Patent
Alston

(10) Patent No.: US 12,383,593 B2
(45) Date of Patent: Aug. 12, 2025

(54) ORGANIC PAIN RELIEF AND HAIR GROWTH COMPOSITION

(71) Applicant: The Tao Talit Corporation, Englewood, NJ (US)

(72) Inventor: Veronica Alston, Cape May CH, NJ (US)

(*) Notice: Subject to any disclaimer, the term of this patent is extended or adjusted under 35 U.S.C. 154(b) by 152 days.

(21) Appl. No.: 17/693,428

(22) Filed: Mar. 14, 2022

(65) Prior Publication Data

US 2022/0401506 A1 Dec. 22, 2022

Related U.S. Application Data

(60) Provisional application No. 63/136,975, filed on Jan. 13, 2021.

(51) Int. Cl.
| | | |
|---|---|---|
| *A61K 36/00* | (2006.01) | |
| *A61K 9/00* | (2006.01) | |
| *A61K 36/53* | (2006.01) | |
| *A61K 36/67* | (2006.01) | |
| *A61K 45/06* | (2006.01) | |

(52) U.S. Cl.
CPC ............ *A61K 36/67* (2013.01); *A61K 9/0014* (2013.01); *A61K 36/53* (2013.01); *A61K 45/06* (2013.01)

(58) Field of Classification Search
CPC .................................................. A61K 9/0014
See application file for complete search history.

(56) References Cited

U.S. PATENT DOCUMENTS

| | | | |
|---|---|---|---|
| 10,245,295 B1 | 4/2019 | Smith | |
| 2018/0303747 A1 | 10/2018 | Higginbotham-Van Horn | |

FOREIGN PATENT DOCUMENTS

| | | | | |
|---|---|---|---|---|
| CN | 107898666 A | 4/2018 | | |
| CN | 108042437 A | 5/2018 | | |
| CN | 108785139 A | 11/2018 | | |
| CN | 109172414 A | 1/2019 | | |
| WO | WO-2013066403 A1 | * | 5/2013 | ............ A01N 31/02 |
| WO | 2017204617 A1 | 11/2017 | | |

OTHER PUBLICATIONS

Santoyo, Chemical composition and antimicrobial activity of *Rosmarinus officinalis* L. essential oil obtained via supercritical fluid extraction. Journal of food protection, (Apr. 2005) vol. 68, No. 4, pp. 790-795 (Year: 2005).*
Diab et al, Chemical composition of Lebanese rosemary (*Rosmarinus officinalis* L.) essential oil as a function of the geographical region and the harvest time. Journal of essential oil research: JEOR (2002), vol. 14, No. 6, pp. 449-452 (Year: 2002).*
Neetu et al, Isolation of Thymol from *Trachyspermum ammi* Fruits for Treatment of Diabetes and Diabetic Neuropathy in STZ-Induced Rats. BioMed research international, (2022) vol. 2022, pp. 8263999 (Year: 2022).*
Adhirajan, et al., "In vivo and in vitro evaluation of hair growth potential of Hibiscus rosa-sinensis Linn.," J. Ethnopharmacol., 2003, vol. 88, Issues 2-3, pp. 235-239.
Al-Harrasi, et al., "Analgesic effects of crude extracts and fractions of Omani frankincense obtained from traditional medicinal plant *Boswellia sacra* on animal models," Asian Pac. J. Trop. Med., 2014, vol. 7S1, pp. S485-S490.
Almohanna, et al., "The Role of Vitamins and Minerals in Hair Loss: A Review," Dermatol. Ther. (Heidelb), 2019, vol. 9, Issue 1, pp. 51-70.
Bansal, et al., "Role of Caffeine in the Management of Androgenetic Alopecia," Int. J. Trichology, 2012, vol. 4, Issue 1, pp. 185-186.
Barreto, et al., "Evidence for the involvement of TNF-$\alpha$ and IL-1$\beta$ in the antinociceptive and anti-inflammatory activity of *Stachys lavandulifolia* Vahl. (Lamiaceae) essential oil and (-)-$\alpha$-bisabolol, its main compound, in mice," J. Ethnopharmacol., 2016, vol. 191, pp. 9-18.
Bartikova, et al., "Antioxidant, pro-oxidant and other biological activities of sesquiterpenes," Curr. Top. Med. Chem., 2014, vol. 14, Issue 22, pp. 2478-2494.
Bó, et al., "Eugenol reduces acute pain in mice by modulating the glutamatergic and tumornecrosis factor $\alpha$ (TNF-$\alpha$) pathways," Fundament. Clin. Pharmacol., 2013, vol. 27, pp. 517-525.
Bonjardim, et al., "Evaluation of the anti-inflammatory and antinociceptive properties of p-cymene in mice," Z Naturforsch C J Biosci, 2012, vol. 67, Issues 1-2, pp. 15-21.
Borhani Haghighi, et al., "Cutaneous application of menthol 10% solution as an abortive treatment of migraine without aura: A randomised, double-blind, placebo-controlled, crossed-over study," Int. J. Clin. Pract., 2010, vol. 64, pp. 451-456.
Bounda, et al., "Review of clinical studies of Polygonum multiflorum Thunb. and its isolated bioactive compounds," Pharmacognosy Res., 2016, vol. 7, Issue 3, pp. 225-236.
Braga, et al., "Antioxidant activity of bisabolol: inhibitory effects on chemiluminescence of human neutrophil bursts and cell-free systems," Pharmacology, 2009, vol. 83, Issue 2, pp. 110-115.
Brewer, "Natural Antioxidants: Sources, Compounds, Mechanisms of Action, and Potential Applications," Comprehensive Revies in Food Science and Food Safety, 2011, vol. 10, Issue 4, pp. 221-247.
Brinkley, et al., "Effect of ginkgo biloba on blood pressure and incidence of hypertension in elderly men and women," Am. J. Hypertens., 2010, vol. 23, Issue 5, pp. 528-533.
Carvalho, A.A. , et al., "Antitumor phenylpropanoids found in essential oils," Biomed. Res. Int., 2015, p. 392674.

(Continued)

*Primary Examiner* — Qiuwen Mi
(74) *Attorney, Agent, or Firm* — INNOVATION CAPITAL LAW GROUP, LLP; Vic Lin

(57) ABSTRACT

A natural supplement is described herein. The supplement includes a therapeutically effective amount of a composition. The composition includes: at least two materials having analgesic activity, at least two materials having anti-inflammatory activity, at least two materials having antioxidant activity, at least two materials having anti-neuralgic activity, at least two materials having blood circulation promotion activity, at least one material having Dihydrotestosterone (DHT) blocking activity, and at least one material having hair thickening activity or hair growth activity. The natural supplement not only provides pain relief from a variety of symptoms, but also promotes hair growth.

17 Claims, 1 Drawing Sheet

(56) References Cited

OTHER PUBLICATIONS

Chen, et al., "Screening of active fractions from Curcuma Longa Radix isolated by HPLC and GC-MS for promotion of blood circulation and relief of pain," J. Ethnopharmacol., 2019, vol. 234, pp. 68-75.
Cho, et al., "Effect of Pumpkin Seed Oil on Hair Growth in Men with Androgenetic Alopecia: A Randomized, Double-Blind, Placebo-Controlled Trial," Evid. Based Complement. Alternat. Med., 2014, p. 549721.
Cloud, et al., "The effect of hawthorn (*Crataegus* spp.) on blood pressure: A systematic review," Advances in Integrative Medicine, 2020, vol. 7, Issue 3, pp. 167-175.
Cohen, "Tulsi-*Ocimum sanctum*: a herb for all reasons," J. Ayurveda Integ. Med., 2014, vol. 5, Issue 4, pp. 251-259.
Dallmeier, et al., "Anesthetic, hypothermic, myorelaxant and anticonvulsant effects of synthetic eugenol derivatives and natural analogues," Pharmacology, 1981, vol. 22, pp. 113-127.
De Almeida,, R.N. et al., "Essential oils and their constituents: Anticonvulsant activity," Molecules, 2011, vol. 16, pp. 2726-2742.
De Cássia da Silveira e Sá, et al., "A Review on Anti-Inflammatory Activity of Phenylpropanoids Found in Essential Oils," Molecules, 2014, vol. 19, Issue 2, pp. 1459-1580.
De Cássia da Silveira e Sá, R. , et al. "Sesquiterpenes from Essential Oils and Anti-Inflammatory Activity," Nat. Prod. Commun., 2015, vol. 10, pp. 1767-1774.
De Cássia da Silveira e Sá, R. , et al., "A review on anti-inflammatory activity of monoterpenes," Molecules, 2013, vol. 18, 1227-1254.
De Santana, et al., "Citronellal, a monoterpene present in Java citronella oil, attenuates mechanical nociception response in mice," Pharmaceutical Biology, 2013, vol. 51, Issue 9, pp. 1144-1149.
De Sousa, D.P. , et al., "A Systematic Review of the Anxiolytic-Like Effects of Essential Oils in Animal Models," Molecules, 2015, 20, pp. 18620-18660.
De Sousa, D.P., "Analgesic-like activity of essential oils constituents," Molecules, 2011, vol. 16, 2233-2252.
De Sousa, D.P., et al., "Pharmacological Activity of (R)-(+)-pulegone, a chemical constituent of essential oils," Z. Naturforsch., 2011, vol. 66, pp. 353-359.
Di Stefano, et al., "Acetyl-L-carnitine in painful peripheral neuropathy: a systematic review," J. Pain Res., 2019, vol. 12, pp. 1341-1351.
Feng, et al., "Eugenol: Antipyretic activity in rabbits," Neuropharmacology, 1987, vol. 26, pp. 1775-1778.
Gohil, et al., "Pharmacological Review on *Centella asiatica*: A Potential Herbal Cure-all," Indian J. Pharm. Sci., 2010, vol. 72, Issue 5, pp. 546-556.
Gottumukkala, et al., "Phytochemical investigation and hair growth studies on the rhizomes of Nardostachys jatamansi DC," Pharmacogn. Mag., 2011, vol. 7, Issue 26, pp. 146-150.
Green, et al., "Menthol desensitization of capsaicin irritation. Evidence of a short-term anti-nociceptive effect," Physiol. Behav., 2000, vol. 68, pp. 631-639.
Guedes da Silva Almeida, et al., "Borneol, a bicyclic monoterpene alcohol, reduces nociceptive behavior and inflammatory response in mice," Sci. World J., 2013, p. 808460.
Habtemariam, "The Therapeutic Potential of Rosemary (*Rosmarinus officinalis*) Diterpenes for Alzheimer's Disease," Evidence-Based Complementary and Alternative Medicine, 2016, pp. 1-14.
Herrera-Ruiz, et al., "The standardized extract of Loeselia mexicana possesses anxiolytic activity through the γ-amino butyric acid mechanism," Journal of Ethnopharmacology, 2011, vol. 138, Issue 2, pp. 261-267.
Higashi, et al., "Efficacy and safety profile of a topical methyl salicylate and menthol patch in adult patients with mild to moderate muscle strain: A randomized, double-blind, parallel-group, placebo-controlled, multicenter study," Clin. Ther., 2010, vol. 32, pp. 34-43.
Huo, et al., "Anti-inflammatory effects of linalool in RAW 264.7 macrophages and lipopolysaccharide-induced lung injury model," J. Surg. Res., 2013, vol. 180(1), pp. e47-e54.
Imtiaz, et al., "Impact of *Trigonella foenum-graecum* Leaves Extract on Mice Hair Growth," Pakistan Journal of Zoology, 2017, vol. 49, Issue 4, pp. 1405-1412.
Jain, et al., "Identification of a new plant extract for androgenic alopecia treatment using a non-radioactive human hair dermal papilla cell-based assay," BMC Complement. Altern. Med., 2016, vol. 16, Issue 8.
Jain, et al., "The wonder of Ayurvedic medicine—Nyctanthes arbortristis," International Journal of Herbal Medicine, 2016, vol. 4, Issue 4, pp. 9-17.
Julian, et al., "B12 as a Treatment for Peripheral Neuropathic Pain: A Systematic Review," Nutrients, 2020, p. 2221.
Kamkaew, et al., "Bacopa monnieri increases cerebral blood flow in rat independent of blood pressure," Phytother. Res., 2013, vol. 27, Issue 1, pp. 135-138.
Katsuyama, et al., "Intraplantar injection of linalool reduces paclitaxel-induced acute pain in mice," Biol. Res., 2012, vol. 33, pp. 175-181.
Kim, et al., "Alpha-Pinene Exhibits Anti-Inflammatory Activity Through the Suppression of MAPKs and the NF-κB Pathway in Mouse Peritoneal Macrophages," Am. J. Chin. Med., 2015, vol. 43, Issue 4, pp. 731-742.
Klein, et al., "Topical application of l-menthol induces heat analgesia, mechanical allodynia, and a biphasic effect on cold sensitivity in rats," Behav. Brain. Res., 2010, vol. 212, pp. 179-186.
Lee, et al., "Hair Growth-Promoting Effects of Lavender Oil in C57BL/6 Mice," Toxicol Res., 2016, vol. 32, Issue 2, pp. 103-108.
Lenardão, et al., "Citronellal as key compound in organic synthesis," Tetrahedron, 2007, vol. 63, pp. 6671-6712.
Li, et al., "α-Pinene, linalool, and 1-octanol contribute to the topical anti-inflammatory and analgesic activities of frankincense by inhibiting COX-2," J. Ethnopharmacol., 2016, vol. 179, 22-26.
Lima, et al., "Anxiolytic-like activity and GC-MS analysis of (R)-(+)-limonene fragrance, a natural compound found in foods and plants," Pharmacol. Biochem. Behav., 2013, vol. 103, Issue 3, pp. 450-454.
Lionnet, et al., "Intrathecal eugenol administration alleviates neuropathic pain in male Sprague-Dawley rats," Phytother. Res., 2010, vol. 24, pp. 1645-1653.
Liu, et al., "Protection by borneol on cortical neurons against oxygen-glucose deprivation/reperfusion: Involvement of anti-oxidation and anti-inflammation through nuclear transcription factor γ B signaling pathway," Neurosci., 2011, vol. 176, pp. 408-419.
Liu, et al., "TRPM8 is the Principal Mediator of Menthol-induced Analgesia of Acute and Inflammatory," Pain, 2013, vol. 154, pp. 2169-2177.
Loussouarn, et al., "Carnosic Acid and Carnosol, Two Major Antioxidants of Rosemary, Act through Different Mechanisms," Plant Physiol., 2017, vol. 175, Issue 3, pp. 1381-1394.
McCarty, et al., "Capsaicin may have important potential for promoting vascular and metabolic health," Open Heart., 2015, vol. 2, Issue 1, p. e000262.
Murugusundram, "Serenoa Repens: Does It have Any Role in the Management of Androgenetic Alopecia?," J. Cutan Aesthet Surg., 2009, vol. 2, Issue 1, pp. 31-32.
Neves, Dina, et al., "A new insight on elderberry anthocyanins bioactivity: Modulation of mitochondrial redox chain functionality and cell redox state," Journal of Functional Foods, 2019, vol. 56, pp. 145-155.
Nieto, et al., "Antioxidant and Antimicrobial Properties of Rosemary (*Rosmarinus officinalis*, L.): A Review," Medicines (Basel), 2018, vol. 5, Issue 3, p. 98.
Ohkubo, et al., "The selective capsaicin antagonista capsazepine abolishes the antinociceptive action of eugenol and guaiacol," J. Dent. Res., 1997, vol. 76, pp. 848-851.
Pan, et al., "Central Mechanisms of Menthol-Induced Analgesia," J. Pharmacol. Exp. Ther., 2012, vol. 343, pp. 661-672.
Panahi, et al., "Rosemary oil vs minoxidil 2% for the treatment of androgenetic alopecia: a randomized comparative trial," Skinmed., 2015, vol. 13, Issue 1, pp. 15-21.

(56) References Cited

OTHER PUBLICATIONS

Park, et al., "Red Ginseng Extract Promotes the Hair Growth in Cultured Human Hair Follicles," J. Med. Food., 2015, vol. 18, Issue 3, pp. 354-362.
Park, et al., "The Analgesic Effects and Mechanisms of Orally Administered," Eugenol. Arch. Pharm. Res., 2011, vol. 34, pp. 501-507.
Patel, et al., "A study on the extracts of Cuscuta reflexa Roxb. in treatment of cyclophosphamide induced alopecia," Daru, 2014, vol. 22, Issue 1, p. 7.
Peana, et al., "Anti-inflammatory activity of linalool and linalyl acetate constituents of essential oils," Phytomedicine, 2002, vol. 9, pp. 721-726.
Peana, et al., "Effects of (-)-linalool in the acute hyperalgesia induced by carrageenan, L-glutamate and prostaglandin E2," Eur. J. Pharmacol., 2004, vol. 497, pp. 279-284.
Peppin, et al., "Capsaicinoids in the treatment of neuropathic pain: a review," Ther. Adv. Neurol. Disord., 2014, vol. 7, Issue 1, pp. 22-32.
Prasad, et al., "Ginger and Its Constituents: Role in Prevention and Treatment of Gastrointestinal Cancer," Gastroenterol. Res. Pract., 2015, p. 142979.
Qui, et al., "Systematic Review and Meta-analysis of the Association Between Metabolic Syndrome and Androgenetic Alopecia" 2021, Published by Medical Journals Sweden, on behalf of the Society for Publication of Acta Dermato-Venereologica, 7 pages.
Quintans-Júnior, et al., "Antinociceptive activity of citronellal in formalin-, capsaicin- and glutamate-induced orofacial pain in rodents and its action on nerve excitability," J Orofac Pain, 2010, vol. 24, pp. 305-312.
Quintans-Júnior, et al., "Phythochemical screening and anticonvulsant activity of *Cymbopogon winterianus* Jowitt (Poaceae) leaf essential oil in rodents," Phytomedicine, 2008, vol. 15, pp. 619-624.
Redman, "Ruscus aculeatus (butcher's broom) as a potential treatment for orthostatic hypotension, with a case report," J. Altern. Complemnet. Med., 2000, vol. 6, Issue 6, pp. 539-549.
Rele, et al., "Effect of mineral oil, sunflower oil, and coconut oil on prevention of hair damage," J Cosmet Sci., 2003, vol. 54 Issue 2, pp. 175-192.
Roberto, et al., "Antioxidant activity of limonene on normal murine lymphocytes: relation to H2O2 modulation and cell proliferation," Basic Clin. Pharmacol. Toxiol., 2010, vol. 160, Issue 1, pp. 38-44.
Rohr, et al., "Upper airway and pulmonary effects of oxidation products of (+)-alpha-pinene, d-limonene, and isoprene in BALB/c mice," Inhal. Toxicol., 2002, vol. 14, Issue 7, pp. 663-684.
Roy, et al., "Effect of Citrullus colocynthis. on Hair Growth in Albino Rats," Journal of PHarmaceuitcal Biology, 2007, vol. 45, Issue 10, pp. 739-744.
Roy, et al., "Hair growth promoting activity of Eclipta alba in male albino rats," Arch. Dermatol. Res., 2008, vol. 300, Issue 7, pp. 357-364.
Rufino, et al., "Evaluation of the anti-inflammatory, anti-catabolic and pro-anabolic effects of E-caryophyllene, myrcene and limonene in a cell model of osteoarthritis," Eur. J. Pharmacol., 2015, vol. 750, pp. 141-150.
Sarmento-Neto, J.F. , et al., "Analgesic Potential of Essential Oils," Molecules, 2015, vol. 21, p. 20.
Semalty, et al., "Semecarpus anacardium Linn.: A review," Pharmacogn. Rev., 2010, vol. 4, Issue 7, pp. 88-94.
Szabadics, et al. "Pre- and post-synaptic effects of eugenol and related compounds on Helix pomatia L. neurons," Acta Biol. Hung., 2000, vol. 51, pp. 265-273.
Tiwari, et al., "Plant derived antioxidants—Geraniol and camphene protect rat alveolar macrophages against t-BHP induced oxidative stress," Toxicology in Vitro, 2009, vol. 23, Issue 2, pp. 295-301.
Vallianou, et al., "Alpha-Lipoic Acid and Diabetic Neuropathy," Rev. Diabet. Stud., 2009, vol. 6, Issue 4, pp. 230-236.
Wallace, "Health Effects of Coconut Oil—A Narrative Review of Current Evidence," J Am Coll Nutr., 2019, vol. 38, Issue 2, pp. 97-107.
Won, et al., "Postischemic hypothermia induced by eugenol protects hippocampal neurons from global ischemia in gerbils," Neurosci. Lett., 1998, vol. 254, pp. 101-104.
Yoon, et al., "Limonene suppresses lipopolysaccharide-induced production of nitric oxide, prostaglandin E2, and pro-inflammatory cytokines in RAW 264.7 macrophages," J. Oleo. Sci., 2010, vol. 59, Issue 8, pp. 415-421.
Yoshimura, et al., "Effect of Pygeum africanum tadenan on micturition and prostate growth of the rat secondary to coadministered treatment and post-treatment with dihydrotestosterone," Urology, 2003, vol. 61, No. 2, pp. 474-478.
Yu, et al., "Preclinical and Clinical Studies Demonstrate That the Proprietary Herbal Extract DA-5512 Effectively Stimulates Hair Growth and Promotes Hair Health," Evid. Based Complement. Alternat. Med., 2017, p. 4395638.
Zhang, et al., "Hair growth-promoting activity of hot water extract of Thuja orientalis," BMC Complement. Altern. Med., 2013, vol. 13, p. 9.
Zhong, et al., "Modulation of LPS-stimulated pulmonary inflammation by borneol in murine acute lung injury model," Inflammation, 2014, vol. 37, pp. 1148-1157.
Zhou, et al., "Soy Phytochemicals and Tea Bioactive Components Synergistically Inhibit Androgen-Sensitive Human Prostate Tumors in Mice," J. Nutr., 2003, vol. 133, No. 2, pp. 516-521.
Zhu, et al., "Curcumin Alleviates Neuropathic Pain by Inhibiting p300/CBP Histone Acetyltransferase Activity-Regulated Expression of BDNF and Cox-2 in a Rat Model," PLoS One, 2014, vol. 9, Issue 2, p. e91303.

\* cited by examiner

NATURAL SUPPLEMENT 100

COMPOSITION 102

MATERIALS HAVING ANALGESIC ACTIVITY 104

MATERIALS HAVING ANTI-INFLAMMATORY ACTIVITY 106

MATERIALS HAVING ANTIOXIDANT ACTIVITY 108

MATERIALS HAVING ANTI-NEURALGIC ACTIVITY 110

MATERIALS HAVING BLOOD CIRCULATION PROMOTION ACTIVITY 112

MATERIALS HAVING DIHYDROTESTOSTERONE (DHT) BLOCKING ACTIVITY 114

MATERIALS HAVING HAIR THICKENING ACTIVITY OR HAIR GROWTH ACTIVITY 116

ORGANIC PAIN RELIEF AND HAIR GROWTH COMPOSITION

CROSS-REFERENCE TO RELATED APPLICATIONS SECTION

This Application is a U.S. Non-Provisional Patent Application that claims priority to U.S. Provisional Patent Application Ser. No. 63/136,975 filed on Jan. 13, 2021, the entire contents of which are hereby incorporated by reference in their entirety.

FIELD OF THE EMBODIMENTS

The field of the invention and its embodiments relate to supplements comprising a therapeutically effective amount of a composition. In particular, the therapeutically effective amount of the composition is effective in alleviating at least one symptom associated with a disease, an illness, or a disorder in a human.

BACKGROUND OF THE EMBODIMENTS

Medications that relieve pain are valuable tools to treat diseases, illnesses, or disorders in humans. Some pain relievers may be purchased in a store without a prescription, such as: acetaminophen, aspirin, ibuprofen, and naproxen, and may be used to treat mild pain or fevers. Aspirin is a non-steroidal anti-inflammatory drug, or NSAID. In addition to pain relief, NSAID's are known to cause stomach ulcers and/or kidney damage.

Other pain relievers need a prescription for use. Opioids are one such example of prescription pain relievers available and may include oxycodone (OxyContin®), hydrocodone (Vicodin®), codeine, morphine, and many others. Opioids may be prescribed to patients who've undergone surgery, a painful injury, or be subjected to a long-term condition, such as cancer. However, opioids cause severe side effects, such as depression, a weakened immune system, and addiction.

Numerous drugs may also be used for hair growth. Signs of hair loss may include: a gradual thinning of ones hair on top of one's head and circular or patchy bald spots. Hair loss may be a sign of age or a symptom of a more serious disorder. Effective treatments for some types of hair loss are available, and such treatments may include: medications, surge to promote hair growth, and laser therapy. Such medications include: minoxidil (e.g., Rogaine), finasteride (Propecia), and others. Hair transplant surgery can be expensive and painful. Possible risks of hair transplant surgery include bleeding and scarring. Moreover, the Food and Drug Administration (FDA) has approved a low-level laser device as a treatment for hereditary hair loss in men and women. However, more studies need to be done to examine and identify the long-term effects of this treatment option. Therefore, what is needed is a natural supplement containing a therapeutically effective amount of a composition that relives pain and also promotes hair growth.

Review of Related Technology:

U.S. Pat. No. 10,245,295 B1 relates to a neurological essential oil composition employing oils containing sesquiterpene compounds that cross the blood-brain barrier, such as Vetiver, Black Pepper, Ginger, Ylang Ylang, Sandalwood, Patchouli, Cedarwood, Myrrh, Frankincense, or Lavender, offering calming relief from seizures, migraine, anxiety tremor, PTSD, and other neurological ailments, minus side-effects often experienced with conventional neurotherapeutics. For neurological stimulation to improve cognitive function, the composition recruits oils such as Coffee, Vanilla, Cinnamon Bark, Clove, Dalmatian Sage, Rosemary, Blood Orange, Lemon, Grapefruit, Peppermint, Lime, Clementine, Spearmint or Coconut. The invention is applied directly to the skin and is also present in other topical administrations such as shampoo, conditioner, lotion, face wash, body wash, bath salts, and in aromatherapy administrations such as candles, nasal inhalers and sprays.

WO 2017/204617 A1 describes a composition for skin and/or hair care and/or treatment. More particularly, the composition comprises seaweed extract, an essential oil with antimicrobial function, where the percentage range of seaweed extract to essential oil are from 2%-80% to 0.1%-10%.

CN108785139A describes haircare and hair-restoring essential oils. The haircare and the hair-restoring essential oil is prepared from the following raw materials in parts by weight: 1 to 3 parts of rosemary essential oil, 3 to 5 parts of rose essential oil, 3 to 8 parts of bergamot essential oil, 5 to 10 parts of tea tree essential oil and 50 to 70 parts of garlic oil.

U.S. Published Patent Application No. 2018/0303747 A1 describes a scalp relieving mixture and spray to alleviate pain on an individual's scalp associated with managing, manipulating, and styling hair on the individual's scalp. The scalp relieving mixture and spray includes pure essential oils, such as clove bud oil, lavender oil, lemongrass oil, peppermint oil, and/or tea tree oil. The scalp relieving mixture also includes *Aloe vera* gel and distilled water.

CN108042437A describes a hair growth conditioning composition. The hair growth conditioning composition is prepared from a hair growth component, an antibacterial agent, and a blood activating agent. The hair growth component is pine needle juice, perfume lotus flower extract, tea tree essential oil, and/or Japanese climbing fern spore extract. The hair growth component is added to the composition to promote hair growth and prevent hair loss. The addition of the antibacterial agent can effectively sterilize and inhibit bacteria. The addition of the blood activating agent can promote blood microcirculation of a scalp, improve the hair follicle environment, and promote hair growth.

CN109172414A describes a hair care essential oil that consists of shea butter, linseed oil, rose grass oil, lemon essential oil, ylang-ylang oil, rosemary oil, ginger extract, ginseng extract, safflower extract, *Prunella vulgaris* extract, and angelica extract. The hair care essential oil helps to thicken hair and address the effects of alopecia.

CN107898666A describes an anti-alopecia shampoo composition with a synergistic effect provided by plant essential oil. The anti-alopecia shampoo composition contains the commonly used components of a shampoo formula, and further contains, by weight, 0.25-0.5% of caffeine and 0.5-3.0% of a high geraniol content plant essential oil composition. The high geraniol content plant essential oil composition can effectively promote the transdermal absorption of caffeine so as to synergistically enhance the refreshing and improve the scalp hair follicle growth activity. With the long-term use of the refreshing anti-alopecia shampoo composition, alopecia can be prevented or reduced.

Various compositions exist. However, their means of operation are substantially different from the present disclosure, as the other inventions fail to solve all the problems taught by the present disclosure.

SUMMARY OF THE EMBODIMENTS

The present invention and its embodiments relate to supplements comprising a therapeutically effective amount of a composition. The therapeutically effective amount of the composition is effective in alleviating at least one symptom associated with a disease, an illness, or a disorder in a human.

A first embodiment of the invention describes a natural supplement comprising a therapeutically effective amount of a composition. The natural supplement is a topical cream configured to be applied to a body of user. The composition includes: at least two materials having analgesic activity, at least two materials having anti-inflammatory activity, at least two materials having antioxidant activity, at least two materials having anti-neuralgic activity, at least two materials having blood circulation promotion activity, at least one material having Dihydrotestosterone (DHT) blocking activity, and at least one material having hair thickening activity or hair growth activity.

In some examples, the at least two materials having analgesic activity include: linalool, 2-methoxy-4-(2-propenyl) phenol, menthol, *Stachys lavandulifolia* Vahl and/or borneol, among others. The at least two materials having anti-inflammatory activity include: a terpene, cadinene, phenylpropanoids, p-Cymene, 2-methoxy-4-(2-propenyl) phenol, and/or citronellal, among other materials. The at least two materials having antioxidant activity include: sesquiterpenes, limonene, eugenyl acetate, a rosemary compound, carsonic acid, phenylpropanoids, 6-methyl-2-(4-methylcyclohex-3-en-1-yl)-hept-5-en-2-ol (Bisabolol), citronellal, camphene, and/or isorosmanol, among other materials.

Moreover, in examples, the at least two materials having anti-neuralgic activity include: capsaicin, Vitamin B12, acetyl L-carnitine, lipoic acid, L-carnitine, and/or curcumin, among other materials. The at least two materials having blood circulation promotion activity include: Vitamin E, Vitamin B, iron, *Bacopa monnieri, Piper nigrum, Ruscus aculeatus, Capsicum annuum, Stellaria media, Zingiber officinale, Centella asiatica, Crataegus, Ginkgo biloba*, and/or *Curcuma longa*, among other materials. The at least one material having DHT blocking activity include: pumpkin seed oil, caffeine, rosemary oil, green tea, saw palmetto, pygeum, lycopene, biotin, stinging nettle, Vitamin B12, and/or Vitamin B6, among other materials. The at least one material having hair thickening activity or hair growth activity include: a coconut oil, a sweet almond oil, a walnut oil, an olive oil, a mineral oil, a jojoba oil, a wheat germ oil, a rosemary oil, a peppermint oil, *Hibiscus rosa sinensis, Bacopa monnieri, Tridax procumbent, Nardostachys jatamansi, Panax ginseng, Emblica officinalis*, Gotu kola, *A. barbadensis* Mill., *Ocimum sanctum, Cuscuta reflexa* Roxb, *Citrullus colocynthis, Eclipta alba, Nyctanthes arbortristis, Trigonella foenum-graecum, Semecarpus anacardium, Thuja orientalis, Loeselia mexicana, Lycium chinense* Mill, and/or *Polygonum multiflorum*, among other materials.

A second embodiment disclosed herein describes a natural supplement comprising a therapeutically effective amount of a composition to promote hair growth. The natural supplement includes at least two materials having anti-inflammatory activity. The at least two materials having anti-inflammatory activity include: a terpene, cadinene, phenylpropanoids, p-Cymene, 2-methoxy-4-(2-propenyl) phenol, and/or citronellal, among other examples not explicitly listed herein. The natural supplement is a topical cream configured to be applied to a scalp of a user.

A third embodiment of the present invention describes an oil comprising a therapeutically effective amount of a composition to reduce pain on a body part of a human the oil is applied to. The oil includes an amount of olive oil, an amount of betel leaf oil, an amount of rosemary oil, and an amount of lavender oil. In examples, the amount of olive oil is about 0.50 L, the amount of betel leaf oil is in a range of about 150 mL to about 350 mL, the amount of rosemary oil is in a range of about 150 mL to about 350 mL, and the amount of lavender oil is in a range of about 50 mL to about 100 mL.

In general, the present invention succeeds in conferring the following benefits and objectives.

The present invention describes a natural supplement comprising a therapeutically effective amount of a composition.

The present invention describes a natural supplement comprising a therapeutically effective amount of a composition, where the therapeutically effective amount of the composition is effective in alleviating at least one symptom associated with a disease, an illness, or a disorder in a human.

The present invention describes a natural supplement comprising a therapeutically effective amount of a composition that serves as a pain reliever, without the negative side effects of some prescription pain killers.

The present invention describes a natural supplement comprising a therapeutically effective amount of a composition that promotes hair growth and/or thickening of hair.

BRIEF DESCRIPTION OF THE DRAWINGS

FIG. 1 depicts a block diagram of the components of a natural supplement, according to at least some embodiments disclosed herein.

DESCRIPTION OF THE PREFERRED EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

As used herein, the singular forms "a," "an," and "the," are intended to include the plural forms as well, unless the context clearly indicates otherwise.

The phrase "and/or," as used herein in the specification and in the claims, should be understood to mean "either or both" of the elements so conjoined, i.e., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

As used herein, a "formulation" may be used interchangeably with a "composition" and/or a "supplement," throughout the specification and refer to the composition as described herein for the relief of the at least one symptom associated with the disease, the illness, or the disorder in the human. The supplement may be in a semi-solid form or a liquid form.

The term "therapeutically effective amount" as used herein refers to its meaning as is generally accepted in the art. The term generally refers to the amount of the formulation that will elicit the requisite biological response in the human. For example, if a given treatment is considered effective when there is at least about a 25% reduction in a measurable parameter associated with a disease or disorder, a therapeutically effective amount of a drug for the treatment of that disease or disorder is that amount necessary to effect at least about a 25% reduction in that parameter.

Terms such as "treating," "treatment," "to treat," "alleviating," or "to alleviate" as used herein refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder (e.g., "preventing" or "to prevent"). Thus, the humans in need of treatment include those already with the disorder, those prone to have the disorder, and those in whom the disorder is to be prevented.

Natural Supplement

A natural supplement 100 is described herein. The natural supplement 100 includes a therapeutically effective amount of a composition 102. The components of the composition 102 are depicted in FIG. 1 and include: at least two materials having analgesic activity 104, at least two materials having anti-inflammatory activity 106, at least two materials having antioxidant activity 108, at least two materials having anti-neuralgic activity 110, at least two materials having blood circulation promotion activity 112, at least one material having Dihydrotestosterone (DHT) blocking activity 114, and at least one material having hair thickening activity or hair growth activity 116. The natural supplement 100 is a topical cream configured to be applied to a body of user. In examples, the natural supplement 100 may be applied to the scalp of the user. In other examples, the natural supplement 100 may be an oil (such as a hair growth oil) applied to the body of the user.

In another example, the natural supplement 100 is described herein. The natural supplement 100 includes a therapeutically effective amount of the composition 102 to promote hair growth. The natural supplement 100 includes at least two materials having anti-inflammatory activity 106.

In a further example, the natural supplement 100 is a tea that comprises at least Borneol and rosemary. In some examples, the tea may additionally comprise elderberries. Elderberry is an important source of redox-active anthocyanins. See, Dina Neves, et al., "A new insight on elderberry anthocyanins bioactivity: Modulation of mitochondrial redox chain functionality and cell redox state," Journal of Functional Foods, 2019, Vol. 56, Pages 145-155, the entire contents of which are hereby incorporated by reference in their entirety.

In another example, the natural supplement 100 is a body bath salt that includes Epsom salt, dead sea salt, and one or more materials described herein. Both the tea and the body bath salt provide medicinal or therapeutic benefits to the user.

In a further example, a body pain oil is described herein. The oil includes a therapeutically effective amount of a composition to reduce pain on a body part of a human the oil is applied to. The oil includes an amount of olive oil, an amount of betel leaf oil, an amount of rosemary oil, and an amount of lavender oil. In examples, the amount of olive oil is about 0.50 L, the amount of betel leaf oil is in a range of about 150 mL to about 350 mL, the amount of rosemary oil is in a range of about 150 mL to about 350 mL, and the amount of lavender oil is in a range of about 50 mL to about 100 mL.

Natural Materials Having Analgesic Properties

As described herein, an "analgesic" is an agent that selectively relieves pain by acting in the central nervous system (CNS) and peripheral pain mediators without changing consciousness. Analgesics may be narcotic or non-narcotic.

Essential oils are traditionally used in aromatherapy, and based on the promising biological properties, pharmacological and clinical studies have demonstrated the profile of these compounds as drug candidates, See, D. P. De Sousa, et al., "Pharmacological Activity of (R)-(+)-pulegone, a chemical constituent of essential oils," Z. Naturforsch., 2011 Vol. 66, Pages 353-359, the entire contents of which are hereby incorporated by reference in their entirety. Several groups have suggested the therapeutic potential of essential oils in multiple areas, including analgesics. See, D. P. De Sousa, "Analgesic-like activity of essential oils constituents," Molecules, 2011, Vol. 16, 2233-2252; Sarmento-Neto, et al., "Analgesic Potential of Essential Oils," Molecules, 2015. Vol. 21, Page 20; R. N. De Almeida, et al., "Essential oils and their constituents: Anticonvulsant activity," Molecules, 2011, Vol. 16, Pages 2726-2742; R De Cassia da Silveira e Sá, et al., "A review on anti-inflammatory activity of monoterpenes," Molecules, 2013, Vol. 18, 1227-1254; R. De Cassia da Silveira e Sá, et al. "Sesquiterpenes from Essential Oils and Anti-Inflammatory Activity," Nat. Prod. Commun., 2015, Vol. 10, Pages 1767-1774; R De Cássia da Silveira e Sá, et al., "A review on anti-inflammatory activity of phenylpropanoids found in essential oils," Molecules, 2014, Vol. 19, 1459-1480; A. A. Carvalho, et al., "Antitumor phenylpropanoids found in essential oils," Biomed. Res. Int., 2015, Page 392674; and D. P. De Sousa, et al., "A Systematic Review of the Anxiolytic-Like Effects of Essential Oils in Animal Models," Molecules, 2015, 20, Pages 18620-18660, the entire contents of which are hereby incorporated by reference in their entirety. Examples of materials having analgesic activity 104 include: linalool, 2-methoxy-4-(2-propenyl) phenol (Eugenol), menthol, *Stachys lavandulifolia* Vahl, and/or borneo, among others.

(−)-Linalool (−)-Linalool is an enantiomer monoterpene present in essential oils of various aromatic plants, such as lavender, rosewood, and bergamot. Linalool possesses several pharmacological activities, including anti-inflammatory, anxiolytic, anticonvulsant, and anti-nociceptive properties. See, S. Katsuyama, et al., "Intraplantar injection of linalool reduces paclitaxel-induced acute pain in mice," Biol. Res., 2012, Vol. 33, Pages 175-181; A. T. Peana, et al., "Anti-inflammatory activity of linalool and linalyl acetate constituents of essential oils," Phytomedicine, 2002, Vol. 9, Pages 721-726; and A. T. Peana, et al., "Effects of (−)-linalool in the acute hyperalgesia induced by carrageenan, L-glutamate and prostaglandin E2," Eur. J. Pharmacol., 2004, Vol. 497, Pages 279-284, the entire contents of which are hereby incorporated by reference in their entirety.

In traditional Chinese medicine, frankincense from *Boswellia carterii* is commonly used for topical treatment of pain and inflammation. See, A. Al-Harrasi, et al., "Analgesic effects of crude extracts and fractions of Omani frankincense obtained from traditional medicinal plant *Boswellia sacra* on animal models," Asian Pac. J. Trop. Med., 2014, Vol. 7S1, Pages S485-S490, the entire contents of which are hereby incorporated by reference in their entirety. A study carried out to investigate the antinociceptive and anti-inflammatory action of frankincense oil and water extracts and three of its main components, i.e., linalool, α-pinene and 1-octanol, via xylene-induced ear edema and a formalin-inflamed hindpaw model in male Kunming mice, showed consistent evidence about their anti-inflammatory and analgesic effects. Frankincense oil extract, which contains more linalool, α-pinene and 1-octanol than frankincense water extract, produced a faster and more effective reduction of the swelling and pain than the water extract. In addition, the combination of linalool, α-pinene, and 1-octanol exhibited stronger biological effect on hindpaw inflammation and COX-2 overexpression than the three compounds used separately, indicating that they contribute to the topical antinociceptive and anti-inflammatory properties of frankincense by inhibiting COX-2 activation. See, X. J. Li, et al., "α-Pinene, linalool, and 1-octanol contribute to the topical anti-inflammatory and analgesic activities of frankincense by inhibiting COX-2," J. Ethnopharmacol., 2016, Vol. 179, 22-26, the entire contents of which are hereby incorporated by reference in their entirety.

Eugenol

Eugenol (or 2-methoxy-4-(2-propenyl) phenol) is a phenylpropanoid that functions as the main constituent of *Eugenia* aromatics (L.) Baill (clove oil, *myrtaceae*), being commonly used as an analgesic and anti-inflammatory in some dental procedures. See, J. Szabadics, et al. "Pre- and post-synaptic effects of eugenol and related compounds on *Helix poniatia* L. neurons," Acta Biol. Hung., 2000, Vol. 51, Pages 265-273; W. D. Bó, et al., "Eugenol reduces acute pain in mice by modulating the glutamatergic and tumornecrosis factor α (TNF-α) pathways," Fundament. Clin. Pharmacol., 2013, Vol. 27, Pages 517-525; T. Ohkubo, et al., "The selective capsaicin antagonista capsazepine abolishes the antinociceptive action of eugenol and guaiacol," J. Dent. Res., 1997, Vol. 76, Pages 848-851; and S. H. Park, et al., "The Analgesic Effects and Mechanisms of Orally Administered," Eugenol. Arch. Pharm. Res., 2011, Vol. 34, Pages 501-507, the entire contents of which are hereby incorporated by reference in their entirety.

Other pharmacological properties of this compound include neuroprotective properties, anticonvulsant properties, antipyretic properties, and reduction of neuropathic and orofacial pain, See, W. H. Won, et al., "Postischemic hypothermia induced by eugenol protects hippocampal neurons from global ischemia in gerbils," Neurosci. Lett., 1998, Vol. 254, Pages 101-104; K. Dallmeier, et al., "Anesthetic, hypothermic, myorelaxant and anticonvulsant effects of synthetic eugenol derivatives and natural analogues," Pharmacology, 1981, Vol. 22, Pages 113-127; J. Feng, et al., "Eugenol: Antipyretic activity in rabbits," Neuropharmacology, 1987, Vol. 26, Pages 1775-1778; and L. Lionnet, et al., "Intrathecal eugenol administration alleviates neuropathic pain in male Sprague-Dawley rats," Phytother. Res., 2010, Vol. 24, Pages 645-1653, the entire contents of which are hereby incorporated by reference in their entirety.

Menthol

Menthol is an analgesic component found in peppermint oil from mint plants, and is found in various commercial products. See, B. Liu, et al., "TRPM8 is the Principal Mediator of Menthol-induced Analgesia of Acute and Inflammatory," Pain, 2013, Vol. 154, Pages 2169-2177, the entire contents of which are hereby incorporated by reference in their entirety. Low to moderate concentrations of topically applied menthol has been shown to inhibit capsaicin irritancy, sprains, heat hypersensitivity and headaches, while high concentrations (topical use or intraplantar injection) generated cold allodynia and hyperalgesia. In addition, patients with neuropathic pain have been reported to also exhibit increased analgesic response induced by menthol. See, B. G. Green, et al., "Menthol desensitization of capsaicin irritation. Evidence of a short-term anti-nociceptive effect," Physiol. Behav., 2000, Vol. 68, Pages 631-639; A. Borhani Haghighi, et al., "Cutaneous application of menthol 10% solution as an abortive treatment of migraine without aura: A randomised, double-blind, placebo-controlled, crossed-over study," Int. J. Clin. Pract., 2010, Vol. 64, Pages 451-456; Y. Higashi, et al., "Efficacy and safety profile of a topical methyl salicylate and menthol patch in adult patients with mild to moderate muscle strain: A randomized, double-blind, parallel-group, placebo-controlled, multicenter study," Clin. Ther., 2010, Vol. 32, Pages 34-43; A. H. Klein, et al., "Topical application of 1-menthol induces heat analgesia, mechanical allodynia, and a biphasic effect on cold sensitivity in rats," Behav. Brain. Res., 2010, Vol. 212, Pages 179-186; and R. Pan, et al., "Central Mechanisms of Menthol-Induced Analgesia," J. Pharmacol. Exp. Ther., 2012, Vol. 343, Pages 661-672, the entire contents of which are hereby incorporated by reference in their entirety.

*Stachys lavandulifolia* Vahl

*Stachys lavandulifolia* Vahl (Lamiaceae) is a plant used in Turkish and Iranian folk medicine as an analgesic and anti-inflammatory agent. One study provided information about the antinociceptive and anti-inflammatory effects displayed by the main compound of *S. lavandulifolia* essential oil, i.e., (−)-α-bisabolol, in models of orofacial nociception. In this study, the data presented in the pain models indicated a stronger effect of (−)-α-bisabolol in comparison with *S. lavandulifolia* essential oil. These findings support the folk use of *S. lavandulifolia* and relates its antinociceptive and anti-inflammatory actions to (−)-α-bisabolol. See, R. S. S. Barreto, et al., "Evidence for the involvement of TNF-α and IL-1β in the antinociceptive and anti-inflammatory activity of *Stachys lavandulifolia* Vahl. (Lamiaceae) essential oil and (−)-α-bisabolol, its main compound, in mice," J. Ethnopharmacol., 2016, Vol. 191, Pages 9-18, the entire contents of which are hereby incorporated by reference in their entirety.

Borneol (BOR)

Borneol (BOR) belongs to the family of bicyclic monoterpene alcohols and is found in the essential oil of several medicinal plants, such as *Lavandula officinalis, Matricaria chamomillia* and *Valeriana officincalis*. See, A. Hattori, et al., "Camphor in the Edo era-camphor and borneol for medicines," Yakushigaku Zasshi, 2000, Vol. 35, Pages 49-54; and W. Zhong, et al., "Modulation of LPS-stimulated pulmonary inflammation by borneol in murine acute lung injury model," Inflammation, 2014, Vol. 37, Pages 1148-1157, the entire contents of which are hereby incorporated by reference in their entirety.

There are three different isomers of BOR, d-(+)-BOR, 1-(−)-BOR, and isoborneol. Natural BOR contains 98% of (+)-BOR. (+)-BOR is broadly employed in food and also used in analgesic and anesthetic preparations in traditional Chinese medicine and Japanese medicine. See, R. Liu, et al., "Protection by borneol on cortical neurons against oxygen-glucose deprivation/reperfusion: Involvement of anti-oxidation and anti-inflammation through nuclear transcription factor γ B signaling pathway," Neurosci., 2011, Vol. 176, Pages 408-419, the entire contents of which are hereby incorporated by reference in their entirety. Recent studies have reported that this monoterpenoid possesses a variety of pharmacological effects, including anti-inflammatory, vasorelaxant, and neuroprotective activities. See, W. Zhong, et al.; R. Liu, et al.; and J. R. G. S. Almeida, et al., "Borneol, a bicyclic monoterpene alcohol, reduces nociceptive behavior and inflammatory response in mice," Sci. World J., 2013, Page 808460, the entire contents of which are hereby incorporated by reference in their entirety.

Natural Materials Having Anti-Inflammatory Properties

Inflammation refers to one's body process of fighting against things that harm it, such as infections, injuries, and toxins, in an attempt to heal itself. The at least two materials having anti-inflammatory activity 106 include: a terpene, cadinene, phenylpropanoids, p-Cymene, 2-methoxy-4-(2-propenyl) phenol (Eugenol), and/or citronellal, among others.

Terpenes

Terpenes are a large and diverse class of organic compounds produced by a variety of plants, particularly conifers, and by some insects. They often have a strong odor and may protect the plants that produce them by deterring herbivores and by attracting predators and parasites of herbivores. Examples of terpenes may include: linalool, citral, camphene, sabinene, citronellol, citronellal, limonene, geraniol, ocimene, borneol, pinene, carvone, myrcene, etc. There are several terpenes that are believed to help alleviate pain by producing anti-inflammatory and analgesic effects.

Linalool is a floral terpene commonly found in perfumes and naturally found in mint, citrus, and lavender. Linalool has anti-inflammatory properties and may be capable of treating inflammatory pain. See, Meixia Huo, et al., "Anti-inflammatory effects of linalool in RAW 264.7 macrophages and lipopolysaccharide-induced lung injury model," J. Surg. Res., 2013, Vol. 180(1), Pages e47-54, the entire contents of which are hereby incorporated by reference in their entirety.

As another example, myrcene is a proven anti-depressant and anti-inflammatory. Myrcene has an effect on the permeability of cell membranes, meaning it acts as a regulator of other terpenes. See, Ana Teresa Rufino, et al., "Evaluation of the anti-inflammatory, anti-catabolic and pro-anabolic effects of E-caryophyllene, myrcene and limonene in a cell model of osteoarthritis," Eur. J. Pharmacol., 2015, Vol. 750, Pages 141-150, the entire contents of which are hereby incorporated by reference in their entirety.

Moreover, pinene is a bicyclic monoterpene chemical compound. There are two structural isomers of pinene found in nature: α-pinene and β-pinene, with both forms being important constituents of pine resin. Alpha-pinene has been found to exhibit anti-inflammatory activity through the suppression of mitogen-activated protein kinases (MAPKs) and the nuclear factor-kappa B (NF-κB) pathway in mouse peritoneal macrophages. See, Dae-Seung Kim, et al., "Alpha-Pinene Exhibits Anti-Inflammatory Activity Through the Suppression of MAPKs and the NF-κB Pathway in Mouse Peritoneal Macrophages," Am. J. Chin. Med., 2015, Vol. 43, Issue 4, Pages 731-742; and Annette C. Rohr, et al., "Upper airway and pulmonary effects of oxidation products of (+)-alpha-pinene, d-limonene, and isoprene in BALB/c mice," Inhal. Toxicol., 2002, Vol. 14, Issue 7, Pages 663-684, the entire contents of which are hereby incorporated by reference in their entirety.

Cadinene

Cadinene is the chemical name of a number of isomeric hydrocarbons that occur in a wide variety of essential oil-producing plants.

Phenylpropanoids

The phenylpropanoids are a diverse family of organic compounds that are synthesized by plants from the amino acids, phenylalanine and tyrosine. Phenylpropanoids are found throughout the plant kingdom, where they serve as essential components of a number of structural polymers, provide protection from ultraviolet light, defend against herbivores and pathogens, and mediate plant-pollinator interactions as floral pigments and scent compounds. Phenylpropanoids have been found to have anti-inflammatory properties. See, Rita de Cássia da Silveira e Sá, et al., "A Review on Anti-Inflammatory Activity of Phenylpropanoids Found in Essential Oils," Molecules, 2011, Vol. 19, Issue 2, Pages 1459-1580, the entire contents of which are hereby incorporated by reference in their entirety.

p-Cymene p-Cymene is a naturally occurring aromatic organic compound and is classified as an alkylbenzene related to a monoterpene. Its structure consists of a benzene ring para-substituted with a methyl group and an isopropyl group. p-Cymene is insoluble in water, but miscible with organic solvents. Some groups have shown the anti-inflammatory properties of p-Cymene in mice. See, Leonardo R. Bonjardim, et al., "Evaluation of the anti-inflammatory and antinociceptive properties of p-cymene in mice," Z Naturforsch C J Biosci, 2012, Vol. 67, Issues 1-2, Pages 15-21, the entire contents of which are hereby incorporated by reference in their entirety.

Citronellal

Citronellal is the major component of the essential oil of *Cymbopogon winterianus* Jowitt (Poaceae) (*Java citronella*) and *C. citrates* (Lemongrass). See, E. J. Lenardão, et al., "Citronellal as key compound in organic synthesis," Tetrahedron, 2007, Vol. 63, Pages 6671-6712, the entire contents of which are hereby incorporated by reference in their entirety. Essential oil obtained from *C. winterianus* (rich in the monoterpenes citronellal, citronellol and citral) demonstrates CNS depressant, anticonvulsant, hypotensive and antinociceptive activities in rodents, See, L. J. Quintans-Júnior, et al., "Phythochemical screening and anticonvulsant activity of *Cymbopogon winterianus* Jowitt (Poaceae) leaf essential oil in rodents," Phytomedicine, 2008, Vol. 15, Pages 619-624, the entire contents of which are hereby incorporated by reference in their entirety.

It was recently demonstrated by several groups that citronellal has antinociceptive and anti-inflammatory effects. See, L. J. Quintans-Júnior, et al., "Antinociceptive activity of citronellal in formalin-, capsaicin- and glutamate-induced orofacial pain in rodents and its action on nerve excitability," J Orofac Pain. 2010, Vol. 24, Pages 305-312, the entire contents of which are hereby incorporated by reference in their entirety. This antinociceptive effect probably occurs through peripheral and central mechanisms, but the exact mechanism of action involved remains to be elucidated, See, Marilia Trindade de Santana, et al., "Citronellal, a monoterpene present in *Java citronella* oil, attenuates mechanical nociception response in mice," Pharmaceutical Biology, 2013. Vol. 51, Issue 9, Pages 1144-1149, the entire contents of which are hereby incorporated by reference in their entirety.

Natural Materials Having Antioxidant Properties

The at least two materials having antioxidant activity include: sesquiterpenes, limonene, eugenyl acetate, a rosemary compound, carsonic acid, phenylpropanoids, 6-methyl-2-(4-methylcyclohex-3-en-1-yl)-hept-5-en-2-ol, citronellal, camphene, and/or isorosmanol, among others not explicitly listed herein.

Sesquiterpenes

Sesquiterpenes, 15-carbon compounds formed from 3 isoprenoid units, are secondary metabolites produced mainly in higher plants, but also in fungi and invertebrates. Sesquiterpenes occur in human food, but they are principally taken as components of many folk medicines and dietary supplements. Recent efforts in the research and development of new drugs derived from natural products have led to the identification of a variety of sesquiterpenes that possess promising anti-inflammatory, antiparasitic and anti-carcinogenic activities, See, Hana Bartikova, et al., "Antioxidant, pro-oxidant and other biological activities of sesquiterpenes," Curr. Top. Med. Chem., 2014 Vol. 14, Issue 22, Pages 2478-2494, the entire contents of which are hereby incorporated by reference in their entirety.

Limonene

Limonene is a monoterpene present in citrus fruit and is used as flavouring agents of foods. It was shown that monoterpenes possess antioxidant activity. Previously, it was demonstrated that limonene exerts anti-proliferative action on a lymphoma cell line without modifying normal lymphocyte viability. Some groups have shown that limonene may protect normal lymphocytes from diseases related to oxidative stress, including cancer, but further research is necessary to establish the role of limonene as a potential antioxidant that can effectively protect lymphocytes from oxidative stress and mitochondrial dysfunction. See, Davicino Roberto, et al., "Antioxidant activity of limonene on normal murine lymphocytes: relation to H2O2 modulation and cell proliferation," Basic Clin. Pharmacol. Toxiol., 2010, Vol. 160, Issue 1, Pages 38-44; and Weon-Jong Yoon, et al., "Limonene suppresses lipopolysaccharide-induced production of nitric oxide, prostaglandin E2, and pro-inflammatory cytokines in RAW 264.7 macrophages," J. Oleo. Sci., 2010, Vol. 59, Issue 8, Pages 415-421; and Naiana G. P. B. Lima, et al., "Anxiolytic-like activity and GC-MS analysis of (R)-(+)-limonene fragrance, a natural compound found in foods and plants," Pharmacol. Biochem. Behav., 2013, Vol. 103, Issue 3, Pages 450-454, the entire contents of which are hereby incorporated by reference in their entirety.

Eugenyl Acetate

Eugenol acetate (Eugenyl acetate), a major phytochemical constituent of some essential oils, exhibits antibacterial, antioxidant, and anti-virulence activities, Rosemary Compound Several studies have reported that rosemary extracts include hepatoprotective, antifungal, insecticide, antioxidant and antibacterial properties. See, Gema Nieto, et al., "Antioxidant and Antimicrobial Properties of Rosemary (*Rosmarinus officinalis*, L.): A Review," Medicines (Basel), 2018, Vol. 5, Issue 3, Page 98; and Solomon Habtemariam, "The Therapeutic Potential of Rosemary (*Rosmarinus officinalis*) Diterpenes for Alzheimer's Disease," Evidence-Based Complementary and Alternative Medicine, 2016, Pages 1-14, the entire contents of which are hereby incorporated by reference in their entirety. Further, one group has analyzed the activities of basil (*Ocimum basilicum* L.) and rosemary (*Rosmarinus officinalis* L.) essential oils against multi-drug resistant clinical strains of *Escherichia coli*. See, Monika Sienkiewicz, et al., "The Potential of Use Basil and Rosemary Essential Oils as Effective Antibacterial Agents," Molecules, 2013, 18, Pages 9334-9351, the entire contents of which are hereby incorporated by reference in their entirety.

Carsonic Acid

Carnosic acid is a natural benzenediol abietane diterpene found in rosemary (*Rosmarinus officinalis*) and common sage (*Salvia officinalis*). Dried leaves of rosemary or sage contain 1.5 to 2.5% carnosic acid. Carnosic acid is used as a preservative or antioxidant in food and non-food products (e.g. toothpaste, mouthwash, and chewing gum) and has been shown to have promising antioxidant properties. See, Margot Loussouarn, et al., "Carnosic Acid and Carnosol, Two Major Antioxidants of Rosemary, Act through Different Mechanisms," Plant Physiol., 2017, Vol. 175, Issue 3, Pages 1381-1394, the entire contents of which are hereby incorporated by reference in their entirety.

6-methyl-2-(4-methylcyclohex-3-en-1-yl)-hept-5-en-2-ol (Bisabolol)

Bisabolol, or more formally α-(−)-bisabolol or also known as levomenol, is a natural monocyclic sesquiterpene alcohol. It is a colorless viscous oil that is the primary constituent of the essential oil from German chamomile (*Matricaria recutita*) and *Myoporum crassifolium*. It is poorly soluble in water and glycerin, but soluble in ethanol. The enantiomer, α-(+)-bisabolol, is also found naturally but is rare. Synthetic bisabolol is usually a racemic mixture of the two, α-(±)-bisabolol. Bisabolol may be used to improve the antioxidant network and restore the redox balance by antagonizing oxidative stress. See, Pier Carlo Braga, et al., "Antioxidant activity of bisabolol: inhibitory effects on chemiluminescence of human neutrophil bursts and cell-free systems," Pharmacology, 2009, Vol. 83, Issue 2, Pages 110-115, the entire contents of which are hereby incorporated by reference in their entirety.

Camphene

Camphene is a bicyclic monoterpene. It is nearly insoluble in water, but very soluble in common organic solvents. Camphene is a minor constituent of many essential oils, such as turpentine, cypress oil, camphor oil, citronella oil, neroli, ginger oil, and valerian, Camphene is used in the preparation of fragrances and as a food additive for flavoring. Camphene has also been shown to be a plant-derived antioxidant. See, M. Tiwari, et al., "Plant derived antioxidants—Geraniol and camphene protect rat alveolar macrophages against t-BHP induced oxidative stress," Toxicology in Vitro, 2009, Vol. 23, Issue 2, Pages 295-301, the entire contents of which are hereby incorporated by reference in their entirety.

Isorosmanol

Rosemary extract consists of phenolic diterpenes such as carnosic acid, carnosol, epirosmanol, and isorosmanol, and phenolic acids, such as ferulic, caffeic, rosmarinic, and chlorogenic acids. Isorosmanol possesses antioxidant, neuroprotective, and neurotrophic effects, and it might be useful in ageing disorders such as the declining of cognitive functions and hyperpigmentation. See, M. S. Brewer, "Natural Antioxidants: Sources, Compounds, Mechanisms of Action, and Potential Applications," Comprehensive Revies in Food Science and Food Safety, 2011, Vol. 10, Issue 4, Pages 221-247, the entire contents of which are hereby incorporated by reference in their entirety.

Natural Materials Having Anti-Neuralgic Properties

Neuralgia is characterized by short, recurring pain in a part of the body or along a specific nerve. The sensation may feel like burning, stabbing or an electric shock. The at least two materials of the natural supplement 100 described herein having anti-neuralgic activity 110 include: capsaicin, Vitamin B12, acetyl L-carnitine, lipoic acid, L-carnitine, and/or curcumin, among others.

Capsaicin is an active component of chili peppers, which are plants belonging to the genus *Capsicum*. It is a chemical irritant for mammals, including humans, and produces a sensation of burning in any tissue with which it comes into contact. See, John F. Peppin, et al., "Capsaicinoids in the treatment of neuropathic pain: a review," Ther. Adv. Neurol. Disord., 2014, Vol. 7, Issue 1, Pages 22-32, the entire contents of which are hereby incorporated by reference in their entirety.

Further, vitamin B12 has been shown as an effective treatment for neuropathic pain. See, Thomas Julian, et al., "B12 as a Treatment for Peripheral Neuropathic Pain: A Systematic Review," Nutrients, 2020, Page 2221, the entire contents of which are hereby incorporated by reference in their entirety, Additionally, Acetyl-L-carnitine (ALC) has shown a neuroprotective effect in patients with peripheral neuropathies of different etiologies. Preclinical studies demonstrated a central anti-nociceptive action, both in neuropathic and nociceptive pain models. See, Giulia Di Stefano, et al., "Acetyl-L-carnitine in painful peripheral neuropathy: a systematic review," J. Pain Res., 2019, Vol. 12, Pages 1341-1351, the entire contents of which are hereby incorporated by reference in their entirety.

Other groups have shown that alpha-lipoic acid seems to delay or reverse peripheral diabetic neuropathy through its multiple antioxidant properties. Treatment with alpha-lipoic acid increases reduced glutathione, an important endogenous antioxidant. See, Natalia Vallianou, et al., "Alpha-Lipoic Acid and Diabetic Neuropathy," Rev. Diabet. Stud., 2009, Vol. 6, Issue 4, Pages 230-236, the entire contents of which are hereby incorporated by reference in their entirety.

Curcumin is a bright yellow chemical produced by *Curcuma longa* plants. It is the principal curcuminoid of turmeric, a member of the ginger family, Zingiberaceae. Additional groups have found that curcumin has played an active role in the treatment of various neurological disorders, such as neuropathic pain. See, Xiaoyan Zhu, et al., "Curcumin Alleviates Neuropathic Pain by Inhibiting p300/CBP Histone Acetyltransferase Activity-Regulated Expression of BDNF and Cox-2 in a Rat Model," PLoS One, 2014, Vol. 9, Issue 2, Page e91303, the entire contents of which are hereby incorporated by reference in their entirety.

Natural Materials that Promote Blood Circulation

Proper blood circulation is a key factor for health and wellness. There are numerous ways to improve blood flow, including diet and lifestyle changes. Materials having blood circulation promotion activity 112 of the natural supplement 100 include: Vitamin E, Vitamin B, iron, *Bacopa monnieri, Piper nigrum, Ruscus aculeatus, Capsicum annuum, Stellaria media, Zingiber officinale, Centella asiatica, Crataegus, Ginkgo biloba*, and/or *Curcuma longa*, among others.

*Bacopa monnieri* is a perennial, creeping herb native to the wetlands of southern and Eastern India, Australia, Europe, Africa. Asia, and North and South America. It is known by the common names water hyssop, waterhyssop, brahmi, thyme-leafed gratiola, herb of grace, and Indian pennywort. *Bacopa monnieri* has been shown to increase blood pressure in rats. See, Natakorn Kamkaew, et al., "*Bacopa monnieri* increases cerebral blood flow in rat independent of blood pressure," Phytother. Res., 2013, Vol. 27, Issue 1, Pages 135-138, the entire contents of which are hereby incorporated by reference in their entirety.

Black pepper (*Piper nigrum*) is a flowering vine in the family Piperaceae, cultivated for its fruit, known as a peppercorn, which is usually dried and used as a spice and seasoning. When fresh and fully mature, the fruit is about 5 mm (0.20 in) in diameter and dark red, and contains a single seed, like all drupes. Peppercorns and the ground pepper derived from them may be described simply as pepper, or more precisely as black pepper (cooked and dried unripe fruit), green pepper (dried unripe fruit), or white pepper (ripe fruit seeds). Piperine, the active substance of black pepper, alleviates hypertension induced by NO synthase inhibition. See, L. Hlavackova, et al., "Piperine, active substance of black pepper, alleviates hypertension induced by NO synthase inhibition," Bratisl Lek. Listy., 2010, Vol. 111, Issue 8, Pages 426-431, the entire contents of which are hereby incorporated by reference in their entirety.

The betel nut includes numerous chemicals, including alkaloids, tannins, flavonoids, triterpenoids, steroids, and fatty acids. See, Xiaoxiao Chen, et al., "Chemical Composition, Pharmacological, and Toxicological Effects of Betel Nut," Evid, Based Complement. Alternat. Med., 2021, PMID No. 34457017, the entire contents of which are hereby incorporated by reference in their entirety. Other researchers have discussed the antioxidant benefits, antibacterial benefits, cytoprotective benefits, cancer preventative effects, and immunomodulatory activity of *Piper betle* or *betel*. See, Nordin Nur Sazwi, et al., "Antioxidant and cytoprotective activities of *Piper betle, Areca catechu, Uncaria gambir* and betel quid with and without calcium hydroxide," BMC Complementary & Alternative Medicine, 2013, Vol. 13, Issue 351, Pages 1-12; Raghavendra. Havale, et al., "Comparative evaluation of pain perception following topical application of clove oil, betel leaf extract, lignocaine gel, and ice prior to intraoral injection in children aged 6-10 years: a randomized control study," J. Dent. Anesth. Pain Med., 2021, Vol. 21, Issue 4, Pages 329-336; Yu-Jen Wu, et al., "(+)-Bornyl p-Coumarate Extracted from Stem of *Piper betle* Induced Apoptosis and Autophagy in Melanoma. Cells," International Journal of Molecular Sciences, 2020, Vol. 21, issue 3737, Pages 1-13; Patrycja Kłos, et al., "Plant-Derived Terpenoids: A Promising Tool in the Fight against Melanoma," Cancers, 2022, Vol. 14, Issue 502, Pages 1-22; Manoj P Rai, et al., "Piper Betel Linn (Betel Vine), the Maligned Southeast Asian Medicinal Plant Possesses Cancer Preventive Effects: Time to Reconsider the Wronged Opinion," Asian Pacific J. Cancer Prev., Vol. 12, Pages 2149-2156; D. G. Kanjwani, et al., "Evaluation of Immunomodulatory Activity of Methanolic Extract of Piper betel," Scand. J. Immunol., 2008, Vol. 67, Issue 6, Pages 589-593; P. Guha, "Betel Leaf: The Neglected Green Gold of India," J. Hum. Ecol., 2006, Vol. 19, Issue 2, pages 87-93;

Sharifah Farhana Syed Ab Rahman, et al., "Chemical composition of *Piper sarmentosum* extracts and antibacterial activity against the plant pathogenic bacteria *Pseudomonas fuscovaginae* and *Xanthomonas oryzae* pv. *oryzae*," Journal of Plant Diseases and Protection, 2014, Vol. 121, Issue 6, Pages 237-242; and Sushma R. Gundala, et al., "Piper Betel Leaf: A Reservoir of Potential Xenohormetic Nutraceuticals with Cancer-Fighting Properties," Cancer Prev. Res., 2014, Vol. 7, issue 5, Pages 477-486, the entire contents of which are hereby incorporated by reference in their entirety.

*Ruscus aculeatus*, known as butcher's-broom, is a low evergreen Eurasian shrub, with flat shoots known as cladodes that give the appearance of stiff, spine-tipped leaves. Small greenish flowers appear in spring, and are borne singly in the centre of the cladodes. The female flowers are followed by a red berry, and the seeds are bird-distributed, but the plant also spreads vegetatively by means of rhizomes. *Ruscus aculeatus* has been shown to have blood circulation promotion activity. See, D. A. Redman. "*Ruscus aculeatus* (butcher's broom) as a potential treatment for orthostatic hypotension, with a case report." J. Altern. Complement. Med., 2000, Vol. 6, Issue 6, Pages 539-549, the entire contents of which are hereby incorporated by reference in their entirety.

*Capsicum anmuum* is a species of the plant genus *Capsicum* (chilies or peppers and capsicums or bell peppers) native to southern North America and northern South America. Capsaicin is used internally for various conditions, including colic and for improving peripheral circulation, and externally for unbroken chilblains. See, Mark F. McCarty, et al., "Capsaicin may have important potential for promoting vascular and metabolic health," Open Heart, 2015, Vol. 2, Issue 1, Page e000262, the entire contents of which are hereby incorporated by reference in their entirety.

*Stellaria media*, chickweed, is an annual and perennial flowering plant in the family Caryophyllaceae. It is native to Eurasia. and naturalized throughout the world. Ginger (*Zingiber officinale*) is a flowering plant whose rhizome, ginger root or ginger, is widely used as a spice and a folk medicine. It is a herbaceous perennial which grows annual pseudostems (false stems made of the rolled bases of leaves) about one meter tall bearing narrow leaf blades. Ginger has been shown to lower blood pressure and improve circulation. See, Sahdeo Prasad, et al., "Ginger and Its Constituents: Role in Prevention and Treatment of Gastrointestinal Cancer," Gastroenterol. Res. Pract., 2015, Page 142979, the entire contents of which are hereby incorporated by reference in their entirety.

*Centella asiatica*, commonly known as Indian pennywort or Asiatic pennywort, is a herbaceous, perennial plant in the flowering plant family Apiaceae. It is native to the wetlands in Asia. It is used as a culinary vegetable and as a medicinal herb. *Centella asiatica* has been widely used as a blood purifier as well as for treating high blood pressure, for memory enhancement and promoting longevity. See, Kashmira J. Gohil, et al., "Pharmacological Review on *Centella asiatica*: A Potential Herbal Cure-all," Indian J. Pharm. Sci., 2010, Vol. 72, Issue 5, Pages 546-556, the entire contents of which are hereby incorporated by reference in their entirety.

*Crataegus*, commonly called hawthorn, quickthorn, thornapple, May-tree, whitethorn, or hawberry, is a genus of several hundred species of shrubs and trees in the family Rosaceae, native to temperate regions of the Northern Hemisphere in Europe, Asia, North Africa, and North America. *Crataegus* is a herbal medicine used for the treatment of cardiovascular disease, particularly congestive heart failure, *Crataegus* is also indicated for the management of hypertension. See, Alexa Cloud, et al., "The effect of hawthorn (*Crataegus* spp.) on blood pressure: A systematic review," Advances in Integrative Medicine, 2020, Vol. 7, Issue 3, Pages 167-175, the entire contents of which are hereby incorporated by reference in their entirety.

*Ginkgo biloba*, commonly known as ginkgo or gingk, also known as the maidenhair tree, is the only living species in the division Ginkgophyta, all others being extinct. *Ginkgo biloba* may have significant antihypertensive properties as well, providing a possible alternative mechanism for cardiovascular disease prevention. See, Tina E. Brinkley, et al., "Effect of *Ginkgo biloba* on blood pressure and incidence of hypertension in elderly men and women," Am. J. Hypertens., 2010, Vol. 23, issue 5, Pages 528-533, the entire contents of which are hereby incorporated by reference in their entirety.

Turmeric is a flowering plant, *Curcuma longa* of the ginger family, Zingiberaceae, the roots of which are used in cooking. The plant is a perennial, rhizomatous, herbaceous plant native to the Indian subcontinent and Southeast Asia, that requires temperatures between 20 and 30° C. (68 and 86° F.) and a considerable amount of annual rainfall to thrive. *Curcuma longa* has been shown to promote blood circulation. See, Zhimin Chen, et al., "Screening of active fractions from *Curcuma longa* Radix isolated by HPLC and GC-MS for promotion of blood circulation and relief of pain," J. Ethnopharmacol., 2019, Vol. 234, Pages 68-75, the entire contents of which are hereby incorporated by reference in their entirety.

Natural Materials having DHT Blocking Activity

Dihydrotestosterone (DHT, 5α-dihydrotestosterone, 5α-DHT, androstanolone or stanolone) is an endogenous androgen sex steroid and hormone. The enzyme 5α-reductase catalyzes the formation of DHT from testosterone in certain tissues including the prostate gland, seminal vesicles, epididymides, skin, hair follicles, liver, and brain. This enzyme mediates reduction of the C4-5 double bond of testosterone. Relative to testosterone, DHT is considerably more potent as an agonist of the androgen receptor (AR). DHT blockers are the most effective hair loss treatment. A study by the American Academy of Dermatology found that finasteride is effective at DHT blocking. See, Areej Adil, et al., "The effectiveness of treatments for androgenetic alopecia: A systematic review and meta-analysis," J. Am. Acad. Dermatol., 2017, Vol. 77, Issue 1, Pages 136-141, the entire contents of which are hereby incorporated by reference in their entirety.

Examples of components having DHT blocking activity 114 include: pumpkin seed oil, caffeine, rosemary oil, green tea, saw palmetto, pygeum, lycopene, biotin, stinging nettle, Vitamin B12, and Vitamin B6. See, Young Hye Cho, et al., "Effect of Pumpkin Seed Oil on Hair Growth in Men with Androgenetic Alopecia: A Randomized, Double-Blind, Placebo-Controlled Trial," Evid. Based Complement. Alternat. Med., 2014, Page 549721; Manish Barisal, et al., "Role of Caffeine in the Management of Androgenetic Alopecia," int. J. Trichology, 2012, Vol. 4, issue 1, Pages 185-186; Yunes Panahi, et al., "Rosemary oil vs minoxidil 2% for the treatment of androgenetic alopecia: a randomized comparative trial," Skinmed, 2015, Vol. 13, Issue 1, Pages 15-21; Jin-Rong Zhou, et al., "Soy Phytochemicals and Tea Bioactive Components Synergistically Inhibit Androgen-Sensitive Human Prostate Tumors in Mice," J. Nutr., 2003, Vol. 133, No. 2, Pages 516-521; Sundaram Murugusundram, "Serenoa Repens: Does It have Any Role in the Management of Androgenetic Alopecia?," J. Cutan Aesthet Surg., 2009, Vol. 2, Issue 1, Pages 31-32; Yosh Yoshimura, et al., "Effect of Pygeum africanum tadenan on micturition and prostate growth of the rat secondary to coadministered treatment and post-treatment with dihydrotestosterone," Urology, 2003, Vol. 61, No. 2, Pages 474-478; and Hind M. Almohanna, et al., "The Role of Vitamins and Minerals in Hair Loss: A Review," Dermatol. Ther. (Heidelb), 2019, Vol. 9, Issue 1, Pages 51-70, the entire contents of which are hereby incorporated by reference in their entirety.

Natural Materials that Promote the Thickening and Growth of Hair

Materials having hair thickening activity or hair growth activity 116 for the natural supplement 100 include: a coconut oil, a sweet almond oil, a walnut oil, an olive oil, a mineral oil, a jojoba oil, a wheat germ oil, a rosemary oil, and/or a peppermint oil, among others. See, B. H. Lee, et al., "Hair Growth-Promoting Effects of Lavender Oil in C57BL/6 Mice," Toxicol Res., 2016, Vol. 32, Issue 2, Pages 103-8; T. C. Wallace, "Health Effects of Coconut Oil-A Narrative Review of Current Evidence," J Am Coll Nutr., 2019, Vol. 38, Issue 2, Pages 97-107; and A. S. Rele, et al., "Effect of mineral oil, sunflower oil, and coconut oil on prevention of hair damage," J Cosmet Sci., 2003, Vol. 54 Issue 2, Pages 175-92. In other examples, the materials having hair thickening activity or hair growth activity 116 for the natural supplement 100 include: *Hibiscus rosa sinensis, Bacopa monnieri, Tridax procumbent, Nardostachys jatamansi, Panax ginseng, Emblica officinalis,* Gotu kola, *A. barbadensis* Mill., *Ocimum sanctum, Cuscuta reflexa* Roxb, *Citrullus colocynthis, Eclipta alba, Nyctanthes arbortristis, Trigonella foenum-graecum, Semecarpus anacardium, Thuja orientalis, Loeselia mexicana, Lycium chinense* Mill, and/or *Polygonum multiflorum*, among others not explicitly listed herein. See, B. H. Lee, et al., "Hair Growth-Promoting Effects of Lavender Oil in C57BL/6 Mice," Toxicol Res., 2016, Vol. 32, Issue 2, Pages 103-8; T. C, Wallace, "Health Effects of Coconut Oil-A Narrative Review of Current Evidence," J Am Coll Nutr., 2019, Vol. 38, Issue 2, Pages 97-107; and A. S. Rele, et al., "Effect of mineral oil, sunflower oil, and coconut oil on prevention of hair damage," J Comet Sci., 2003, Vol. 54 Issue 2, Pages 175-92, the entire contents of which are hereby incorporated by reference in their entirety.

*Hibiscus rosy sinensis* is a species of tropical hibiscus, a flowering plant in the Hibisceae tribe of the family Malvaceae. *Hibiscus rosa sinensis* has been shown to have hair growth potential. *Bacopa monnieri* is a perennial, creeping herb native to the wetlands of southern and Eastern India, Australia, Europe, Africa, Asia, and North and South America. *Tridax procumbens* is a species of flowering plant in the daisy family. It is best known as a widespread weed and pest plant. It is native to the tropical Americas, but it has been introduced to tropical, subtropical, and mild temperate regions worldwide. *Nardostachys jatamansi* is a flowering plant of the valerian family that grows in the Himalayas. It is a source of a type of intensely aromatic amber-colored essential oil, spikenard.

*Panax ginseng* is a species of plant whose root is the original source of ginseng. It is a perennial plant that grows in the mountains of East Asia. *Phyllanthus emblica*, also known as emblic, emblic myrobalan, myrobalan, Indian gooseberry, Malacca tree, or amla from Sanskrit amalaki is a deciduous tree of the family Phyllanthaceae. *Centella asiatica*, commonly known as Indian pennywort, Asiatic pennywort, or Gotu kola, is a herbaceous, perennial plant in the flowering plant family Apiaceae. *Aloe vera* or *A. barbadensis* Mill. is a succulent plant species of the genus *Aloe*. An evergreen perennial, it originates from the Arabian Peninsula, but grows wild in tropical, semi-tropical, and arid climates around the world. *Ocimum tenuiflorum*, commonly known as holy basil or tulsi, is an aromatic perennial plant in the family Larniaceae. It is native to the Indian subcontinent and widespread as a cultivated plant throughout the Southeast Asian tropics. *Cuscuta reflexa* Roxb. (Family Cuscutaceae), known as "amarvela" in vernacular, is a parasite, with slender yellow stems. It is widespread in temperate and tropical regions and commonly found throughout India. It grows on different host plants. Traditionally, it used in treatment of protracted fever, diaphoretic, and as demulcent and as purgative.

*Citrullus colocynthis*, with many common names including colocynth, bitter apple, bitter cucumber, desert gourd, egusi, vine of Sodom, or wild gourd, is a desert viny plant native to the Mediterranean Basin and Asia, especially Turkey, and Nubia. *Eclipta prostrata* commonly known as false daisy, yerba de tago, Karisalankanni, and bhringraj, is a species of plant in the sunflower family. It is widespread across much of the world.

*Nyctanthes arbor-tristis*, the night-flowering jasmine or Parijat or hengra bubar or Shiuli is a species of *Nyctanthes* native to South Asia and Southeast Asia. *Nyctanthes arbortristis* is a shrub or a small tree growing to 10 m tall, with flaky grey bark. Fenugreek (*Trigonella foenum-graecum*) is an annual plant in the family Fabaceae, with leaves consisting of three small obovate to oblong leaflets. It is cultivated worldwide as a semiarid crop. *Semecarpus anacardium*, commonly known as the marking nut tree, phobi nut tree and varnish tree, is a native of India, found in the outer Himalayas to the Coromandel Coast.

*Thuja orientalis* is a distinct genus of evergreen coniferous tree in the cypress family Cupressaceae and is distributed widely in China, Japan, and Korea. It has been traditionally used to promote hair growth in the oriental medicine. While *T. occidentalis* (Western *T. orientalis*) was found to contain a strong 5α-reductase inhibitor that suppresses the peripheral conversion of testosterone into dihydrotestosterone (DHT), it was reported that flavonoid and diterpene from *T. orientalis* can be used as 5α-reductase inhibitors for treating androgen-related diseases. *Loeselia mexicana* is a woody perennial member of the phlox family. *Lycium chinense* is one of two species of boxthorn shrub in the family Solanaceae. *Reynoutria multiflora* is a species of flowering plant in the buckwheat family Polygonaceae.

Support for the hair thickening activity or hair growth activity for the natural supplement 100 of *Hibiscus rosa sinensis, Bacopa monnieri, Tridax procumbent, Nardostachys jatamansi, Panax ginseng, Emblica officinalis,* Gotu kola, *A. barbadensis* Mill., *Ocimum sanctum, Cuscuta reflexa* Roxb, *Citrullus colocynthis, Eclipta alba, Nyctanthes arbortristis, Trigonella foenum-graecum, Semecarpus anacardium, Thuja orientalis, Loeselia mexicana, Lycium chinense* Mill, and/or *Polygonum multiflorum*, may be found, at least, in: N. Adhirajan, et al., "In vivo and in vitro evaluation of hair growth potential of *Hibiscus rosa-sinensis* Linn.," J. Ethnopharmacol., 2003. Vol. 88, Issues 2-3, Pages 235-9; Ruchy Jain, et al., "Identification of a new plant extract for androgenic alopecia treatment using a nonradioactive human hair dermal papilla cell-based assay," BMC Complement. Altern. Med., 2016, Vol. 16, Issue 8; Disha Prajapati, "Evaluation of *Tridax procumbens* as promising hair growth promoter," international Journal of Pharmaceutical Research, 2021, Vol. 13, Issue 1; Venkateswara Rao Gottumukkala, et al., "Phytochemical investigation and hair growth studies on the rhizomes of *Nardostachys jatamansi* DC," Pharmacogn. Mag., 2011, Vol. 7, Issue 26, Pages 146-150; Gyeong-Hun Park, et al., "Red Ginseng Extract Promotes the Hair Growth in Cultured Human Hair Follicles," J. Med. Food, 2015. Vol. 18, Issue 3, Pages 354-362; Jae Young Yu, et al., "Preclinical and Clinical Studies Demonstrate That the Proprietary Herbal Extract DA-5512 Effectively Stimulates Hair Growth and Promotes Hair Health," Evid, Based Complement. Alternat. Med., 2017, Page 4395638; Yeong Min Choi, et al., "Titrated extract of Centella asiatica increases hair inductive property through inhibition of STAT signaling pathway in three-dimensional spheroid cultured human dermal papilla cells," Biosci. Biotechnol. Biochem., 2017, Vol. 81, Issue 12, Pages 2323-2329; Marc Maurice Cohen, "Tulsi-Ocimum sanctum a herb for all reasons," J. Ayurveda Integ. Med., 2014, Vol. 5, Issue 4, Pages 251-259; Satish Patel, et al., "A study on the extracts of Cuscuta reflexa Roxb. in treatment of cyclophosphamide induced alopecia," Daru, 2014, Vol. 22, Issue 1, Page 7; R. K. Roy, et al., "Effect of Citrullus colocynthis on Hair Growth in Albino Rats," Journal of PHarmaceutical Biology, 2007, Vol. 45, Issue 10, Pages 739-744; R. K. Roy, et al., "Hair growth promoting activity of Eclipta alba in male albino rats," Arch. Dermatol. Res., 2008, Vol. 300, Issue 7, Pages 357-364; Pushpendra Kumar Jain, et al., "The wonder of Ayurvedic medicine—Nyctanthes arbortristis," International Journal of Herbal Medicine, 2016, Vol. 4, Issue 4, Pages 9-17; Fariha Imtiaz, et al., "Impact of Trigonella foenum-graecum Leaves Extract on Mice Hair Growth," Pakistan Journal of Zoology, 2017, Vol. 49, Issue 4, Pages 1405-1412; Mona Semalty, et al., "Semecarpus anacardium Linn.: A review," Pharmacogn. Rev., 2010, Vol. 4, Issue 7, Pages 88-94; Nan-nan Zhan, et al., "Hair growth-promoting activity of hot water extract of Thuja orientalis," BMC Complement. Altern. Med., 2013, Vol. 13, Page 9; Maribel Lucila, et al., "The standardized extract of Loeselia mexicana possesses anxiolytic activity through the γ-amino butyric acid mechanism," Journal of Ethnopharmacology, 2011, Vol. 138, Issue 2, Pages 261-267; and Guy-Armel Bounda, et al., "Review of clinical studies of Polygonum multiflorum Thunb. and its isolated bioactive compounds," Pharmacognosy Res., 2016, Vol. 7, issue 3, Pages 225-236, the entire contents of which are hereby incorporated by reference in their entirety.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others or ordinary skill in the art to understand the embodiments disclosed herein.

When introducing elements of the present disclosure or the embodiments thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A natural supplement comprising a therapeutically effective amount of a composition, the composition comprising:
   at least two materials having analgesic activity;
   at least two materials having anti-inflammatory activity;
   at least two materials having antioxidant activity;
   at least two materials having anti-neuralgic activity;
   at least two materials having blood circulation promotion activity;
   at least one material having Dihydrotestosterone (DHT) blocking activity; and
   at least one material having hair thickening activity or hair growth activity, wherein:
   the at least two materials having anti-neuralgic activity are selected from the group consisting of: capsaicin, Vitamin B12, acetyl L-carnitine, lipoic acid, L-carnitine, and curcumin; and
   the natural supplement is a topical cream configured to be applied to a body of a user.

2. The natural supplement of claim 1, wherein the at least two materials having analgesic activity are selected from the group consisting of: linalool, 2-methoxy-4-(2-propenyl) phenol, menthol, Stachys lavandulifolia Vahl and borneol.

3. The natural supplement of claim 1, wherein the at least two materials having anti-inflammatory activity are selected from the group consisting of: a terpene, cadinene, phenylpropanoids, p-Cymene, 2-methoxy-4-(2-propenyl) phenol, and citronellal.

4. The natural supplement of claim 1, wherein the at least two materials having antioxidant activity are selected from the group consisting of: sesquiterpenes, limonene, eugenyl acetate, a rosemary compound, carsonic acid, phenylpropanoids 6-methyl-2-(4-methylcyclohex-3-en-1-yl)-hept-5-en-2-ol (Bisabolol), citronellal, camphene, and isorosmanol.

5. The natural supplement of claim 1, wherein the at least two materials having blood circulation promotion activity are selected from the group consisting of: Vitamin F, Vitamin B, iron, Bacopa monnieri, Piper nigrum, Ruscus aculeatus, Capsicum annuum, Stellaria media, Zingiber officinale, Centella asiatica, Crataegus, Ginkgo biloba, and Curcuma longa.

6. The natural supplement of claim 1, wherein the at least one material having DHT blocking activity is selected from the group consisting of: pumpkin seed oil, caffeine, rosemary oil green tea, saw palmetto, pygeum, lycopene, biotin, stinging nettle, Vitamin B12, and Vitamin B6.

7. The natural supplement of claim 1, wherein the at least one material having hair thickening activity or hair growth activity is selected from the group consisting of: a coconut oil, a sweet almond oil, a walnut oil, an olive oil, a mineral oil, a jojoba oil, a wheat germ oil, a rosemary oil, a peppermint oil, Hibiscus rosa sinensis, Bacopa monnieri, Tridax procumbent, Nardostachys jatamansi, Panax ginseng, Emblica officinalis, Gotu kola, A. barbadensis mill., Ocimum sanctum, Cuscuta reflexa roxb, Citrullus colocynthis, Eclipta alba, Nyctanthes arbortristis, Trigonella foenum-graecum, Semecarpus anacardium, Thuja orientalis, Loeselia mexicana, Lycium chinense mill, and Polygonum multiflorum.

8. The natural supplement of claim 1, wherein the at least two materials having analgesic activity further comprises an oil selected from the group consisting of
   an amount of olive oil;
   an amount of betel leaf oil;

an amount of rosemary oil; and
an amount of lavender oil.

9. The natural supplement of claim 8, wherein the oil is present in the topical cream configured to be applied to a scalp of the user.

10. The natural supplement of claim 8, wherein the oil further comprises one or more of a coconut oil, a sweet almond oil, a walnut oil, a mineral oil, a jojoba oil, a wheat germ oil, and/or a peppermint oil.

11. A natural supplement comprising a therapeutically effective amount of a composition, the composition comprising:
    at least two materials having analgesic activity;
    at least two materials having anti-inflammatory activity;
    at least two materials having antioxidant activity;
    at least two materials having anti-neuralgic activity;
    at least two materials having blood circulation promotion activity;
    at least one material having Dihydrotestosterone (DHT) blocking activity; and
    at least one material having hair thickening activity or hair growth activity, wherein:
    the at least two materials having anti-neuralgic activity are selected from the group consisting of: capsaicin, Vitamin B12, acetyl L-carnitine, lipoic acid, L-carnitine, and curcumin; and
    the at least two materials having analgesic activity further comprises an oil selected from the group consisting of:
    an amount of olive oil;
    an amount of *betel* leaf oil;
    an amount of rosemary oil; and
    an amount of lavender oil; and
    the oil is present in a topical cream configured to be applied to a scalp of a user.

12. The natural supplement of claim 11, wherein the at least two materials having analgesic activity are selected from the group consisting of: linalool, 2-methoxy-4-(2-propenyl) phenol, menthol, *Stachys lavandulifolia* Vahl and borneol.

13. The natural supplement of claim 11, wherein the at least two materials having anti-inflammatory activity are selected from the group consisting of: a terpene, cadinene, phenylpropanoids, p-Cymene, 2-methoxy-4-(2-propenyl) phenol, and citronellal.

14. The natural supplement of claim 11, wherein the at least two materials having antioxidant activity are selected from the group consisting of: sesquiterpenes, limonene, eugenyl acetate, a rosemary compound, carsonic acid, phenylpropanoids 6-methyl-2-(4-methylcyclohex-3-en-1-yl)-hept-5-en-2-ol (Bisabolol), citronellal, camphene, and isorosmanol.

15. The natural supplement of claim 11, wherein the at least two materials having blood circulation promotion activity are selected from the group consisting of: Vitamin F, Vitamin B, iron, *Bacopa monnieri*, *Piper nigrum*, *Ruscus aculeatus*, *Capsicum annuum*, *Stellaria media*, *Zingiber officinale*, *Centella asiatica*, *Crataegus*, *Ginkgo biloba*, and *Curcuma longa*.

16. The natural supplement of claim 11, wherein the at least one material having DHT blocking activity is selected from the group consisting of: pumpkin seed oil, caffeine, rosemary oil green tea, saw palmetto, pygeum, lycopene, biotin, stinging nettle, Vitamin B12, and Vitamin B6.

17. The natural supplement of claim 11, wherein the at least one material having hair thickening activity or hair growth activity is selected from the group consisting of: a coconut oil, a sweet almond oil, a walnut oil, an olive oil, a mineral oil, a jojoba oil, a wheat germ oil, a rosemary oil, a peppermint oil, *Hibiscus rosa sinensis*, *Bacopa monnieri*, *Tridax procumbent*, *Nardostachys jatamansi*, *Panax ginseng*, *Emblica officinalis*, Gotu kola, *A. barbadensis* mill., *Ocimum sanctum*, *Cuscuta reflexa* roxb, *Citrullus colocynthis*, *Eclipta alba*, *Nyctanthes arbortristis*, *Trigonella foenum-graecum*, *Semecarpus anacardium*, *Thuja orientalis*, *Loeselia mexicana*, *Lycium chinense* mill, and *Polygonum multiflorum*.

\* \* \* \* \*